United States Patent [19]

Brewer et al.

[11] Patent Number: 4,659,667

[45] Date of Patent: Apr. 21, 1987

[54] PROCESS TO RECOVER CRYSTALLINE ENZYMES AND CRYSTALLINE ENZYMES PRODUCED THEREBY

[75] Inventors: Jack W. Brewer; Chong Y. Kim, both of Elkhart, Ind.

[73] Assignee: Miles Laboratories, Inc., Elkhart, Ind.

[21] Appl. No.: 735,971

[22] Filed: May 20, 1985

Related U.S. Application Data

[63] Continuation-in-part of Ser. No. 705,556, Jan. 26, 1985, abandoned.

[51] Int. Cl.$^4$ .......................... C12N 9/56; C12N 9/00; C12N 9/28; C12N 9/54; C12R 1/10
[52] U.S. Cl. .................... 435/222; 435/183; 435/202; 435/221; 435/814; 435/836
[58] Field of Search ............... 435/814, 183, 202, 221, 435/222

[56] References Cited

PUBLICATIONS

Nesterenko et al, Biological Abstracts, vol. 73, No. 5, 31523, (1981).
Branchini et al, Analytical Biochemistry, vol. 104, No. 2, pp. 386–396, (1980).
Ohta et al, Agricultural and Biological Chemistry, vol. 48, No. 4, pp. 903–908, (1984).

*Primary Examiner*—Lionel M. Shapiro
*Attorney, Agent, or Firm*—Jerome L. Jeffers

[57] ABSTRACT

This invention relates to a novel process for the recovery of enzyme crystals. The enzymes may be obtained from any enzyme-producing microorganisms such as bacteria, fungi, and yeasts. The invention contemplates supersaturation and/or crystallization to obtain enzymes in the crystalline form, and is particularly effective for the recovery of heat stable alpha-amylase in a crystal form.

6 Claims, 1 Drawing Figure

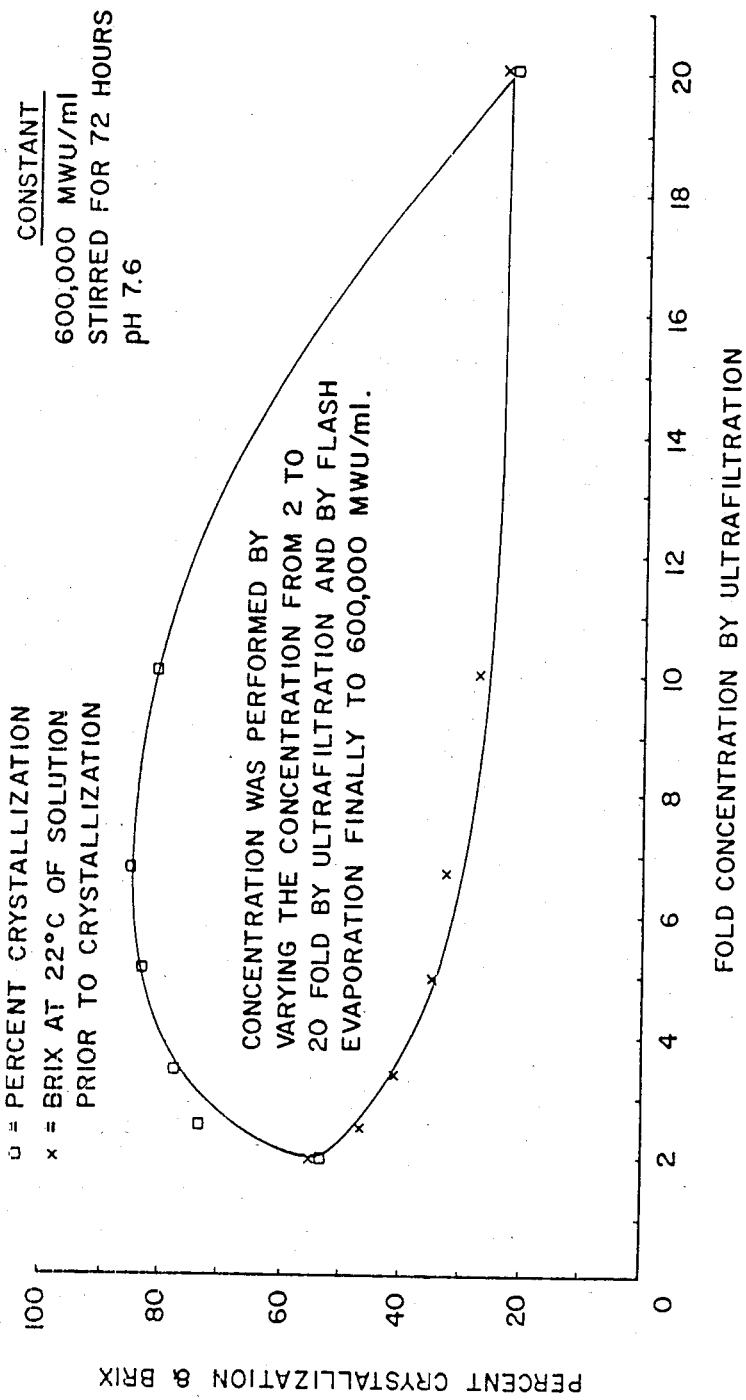

PROCESS TO RECOVER CRYSTALLINE ENZYMES AND CRYSTALLINE ENZYMES PRODUCED THEREBY

This application is a continuation-in-part of copending application Ser. No. 705,556 filed Feb. 26, 1985, now abandoned.

This invention relates to a novel process for the recovery of a crystalline form of enzymes produced by enzyme-producing microorganisms, such as bacteria, fungi, and yeasts, and to enzyme crystals recovered by this process. More particularly, the invention contemplates supersaturation techniques to obtain enzyme crystals. The invention is particularly effective for the recovery of alkaline protease and heat stable alpha-amylase in a crystalline form.

BACKGROUND OF THE INVENTION

Enzymes behave as biocatalysts, regulating many of the chemical reactions that naturally occur in living organisms. When isolated, enzymes also have many industrial, as well as medical uses. For instance, enzymes are used in the tanning, food and detergent industries.

Much research has been conducted on methods to precipitate enzymes. For instance, Chiang, Alter, and Sternberg, "Purification and Characterization of a Thermostable Alpha-Amylase from *Bacillus licheniformis*", Starke, Vol. 31, No. 3, pages 86–92, (1979) disclose ammonium sulfate precipitation of TAKA-THERM ®, a trademark of Miles Laboratories, Inc., Elkhart, Ind. for carbohydrase enzymes. In this reference, the TAKA-THERM used was alpha-amylase isolated from *Bacillus licheniformis* BLM 1777. The precipitation was followed by cellulose chromatography purification. Next, fractions were combined and concentrated by ultrafiltration. The enzyme concentrate was then dialized and then ammonium sulfate was added until turbidity (the beginning of precipitation) occurred.

Dixon et al., "Enzymes", Academic Press, 3rd edition, pages 1–40, (1979) discuss ammonium sulfate crystallization of enzymes and a variation of this method involving extracting a small amount of the precipitated enzyme with cold, dilute ammonium sulfate solutin.

Yokoyama et al., "Production and Crystallization of Acid Carboxypeptidase of *Penicillium janthinellum* and Mode of Action on Peptides and Proteins, and Anti-Inflammatory Activities of the Enzyme", *Amino Acid Nucleic Acid*, Vol. 35, pages 64–75 (1977) discuss combining column chromatography with ammonium sulfate precipitation for recovery of acid carboxypeptidase.

Uwajima et al., "Production, Purification and Crystallization of Creatinine Deiminase of *Corynebacterium lilium*", Studies on Creatinine Metabolism by Microorganisms, Part II, Tokyo Research Laboratory, Kyowa Hakko Kogyo Company, Ltd., Machida-shi, Tokyo, Agric. Biol. Chem., 41(2) (1977) pages 339–344 disclose a method to obtain crystallized creatinine deiminase consisting of ammonium sulfate fractionation, protamine treatment, and cellulose chromatography.

Uwajima et al., "Production, Purification and Crystallization of III Alpha-Hydroxysteroid Dehydrogenase of *Pseudomonas Putrida*", Tokyo Research Laboratory, Kyowa Hakko Kogyo Company, Ltd., Machida-shi, Tokyo, *Agric. Biol. Chem.*, Vol. 42, No. 8, pages 1577–1583, (1978) disclose a method to obtain dehydrogenase involving fractionation with ammonium sulfate and column chromatography on DEAE-cellulose, Sephadex G-100 and hydroxylapatite.

McCary in U.S. Pat. No. 3,642,582 discloses a process to obtain alpha-amylase involving first removing polyvalent anions from alpha-amylase preparations, and then contacting the preparation with fibrous alumina.

STATEMENT OF INVENTION

The present invention provides for a method for the recovery of an enzyme from a solution thereof obtained from an enzyme-producing micro-organism, said method comprising:
(a) concentrating to supersaturation the enzyme-containing solution, said super-saturated concentrate having a pH in a range near the isoelectric point of the enzyme,
(b) inducing crystallization, and
(c) recovering an enzyme crystal final product.

OBJECT AND ADVANTAGES OF THE PRESENT INVENTION

The object of the present invention is the recovery of enzymes in a crystal form. The invention is a simplification over known methods to obtain enzyme crystals in that the enzyme-containing solution prior to the induction of crystallization is not required to be pure, i.e. free of essentially all soluble solids. Also, in the prior art, salts or organic solvents are introduced to induce crystallization of enzymes, which may be done but is unnecessary in the present invention. When salts and/or organic solvents are employed in the prior art methods to induce an enzyme complex to precipitate, often the precipitate is not used as the end product but only as a step in an overall process that results in a liquid end product. Thus, the supersaturation techniques of the present invention eliminate many problems associated with the typical industrial enzyme-containing liquid products, such as product stability, microbial contamination, low potency, large volume, and high transportation costs.

BRIEF DESCRIPTION OF THE DRAWING

The drawing is a graphic depiction of an embodiment of the invention where the enzyme is alpha-amylase (TAKA-THERM). In the graph, the Brix value and percent crystallization are compared to the fold concentration.

GENERAL DESCRIPTION OF THE INVENTION

The present invention begins with an enzyme-containing solution. The solution containing the enzyme may be obtained from any enzyme-producing microorganism. Thus, the enzyme may be extracellular or intracellular. Any of various known methods for removing the biomass, cell fragments, insoluble solids, and the like, may be employed.

Preferably, the enzyme is a fermentation product. For instance, alpha-amylase may be obtained from *Bacillus amyloliquifaciens* under controlled fermentation and alkaline protease may be obtained from *Bacillus subtilis* under controlled fermentation. In the most preferred embodiment, the enzyme is heat stable alpha-amylase obtained from the fermentation of *Bacillus licheniformis*. Known methods such as centrifugation may be used to remove the biomass, providing a solution that is a cell-free filtrate containing the enzyme. Thus, in the preferred method, the enzyme-containing solution is a cell-free filtrate obtained from the controlled fermentation of an enzyme-secreting bacteria.

Next, the process of the present invention contemplates supersaturation techniques in concentrating the enzyme-containing solution. Optionally, the enzyme-containing solution may be first diluted with water, and the dilution followed by supersaturation techniques in concentrating the solution. A supersaturated solution is one which has a greater amount of solute than is normally possible for the saturated solution at that temperature, and such supersaturated solutions are unstable. A sudden shock, dust particles, or a scratch on the inner surface of the solution's container can act as a center on which crystallization may begin. Thus, care must be taken to maintain the supersaturated condition until it is desired to have crystallization begin. See, Pierce, Sawyer, and Haenisch, "Quantitative Analysis", 4th Edition, page 349 (Jan. 1961).

Desirably, supersaturation is achieved by any combination of ultrafiltration (UF) and/or evaporation. Preferably, UF is conducted at 5° C. to 15° C. until the volume is about 10% to 50% of the volume of the original enzyme-containing solution. This may be a sufficient extent of concentration to achieve supersaturation; however, in a more desirable embodiment UF is followed by evaporation.

It is desirable to conduct the evaporation under a vacuum at a temperature between 25° C. and 39° C. until the concentrate is supersaturated. In the preferred method, the evaporation under a vacuum is conducted at 32° C., at a pressure differential of approximately 20 to 30 inches of mercury. The evaporation under vacuum should be continued until the volume of the concentrate is approximately 10% to 20% of its volume after ultrafiltration.

The concentration creates a supersaturated state in the solution, in which the Brix value reading should be approximately 8% to 60% at 22° C. The Brix value indicates the amount of soluble solids in solution in relation to sucrose as a standard. In an embodiment with alpha-amylase, the Brix value is between about 30% and 40% at 22° C. In another embodiment with alkaline protease, the Brix value is between about 8% and 12% at 20° C.

In a preferred embodiment with alpha-amylase, concentration is begun by UF to about 25-50% of the volume of the original enzyme-containing solution, and then continued by evaporation. In another embodiment with alkaline protease, UF may be continued until the volume is down to approximately 10%-15% of the original enzyme-containing solution with no evaporation following. However, in a preferred embodiment with alkaline protease, UF is followed by evaporation.

The pH must be at a level near the isoelectric point of the enzyme. The pH should be in a range from about 2.5 pH units below the isoelectric point up to about 2.5 pH units above the isoelectric point. Preferably, the pH is in a range ±1.5 units from the isoelectric point. In the preferred embodiments, in which the enzyme is obtained from the fermentation of enzyme-secreting bacteria, the pH adjustment during the fermentation process may have been sufficient. Accordingly, prior to concentrating to supersaturation, the pH of the original enzyme-containing solution may already be in the desired range near the isoelectric point of the enzyme. Thus, further pH adjustment may be unnecessary. On the other hand, if the pH is not already in the desired range near the isoelectric point of the enzyme, then sometime during or after concentration, the pH must be adjusted to a point within the desired range. Also, even though the pH may already be in the desired range, it may be adjusted either nearer or even farther from the isoelectric point, as long as it is at a point within the desired range. For alpha-amylase, the pH should be between 6.8 and 8.1, and for alkaline protease the pH should be between 8.0 and 10.0. The isoelectric point of alpha-amylase is approximately 7.2 and for alkaline protease is approximately 9.0. Typically, ammonia or KOH is used for pH adjustment.

After concentration, crystallization is induced. Sometimes the movement during UF and/or evaporation is enough to cause crystallization to begin spontaneously when concentrating is terminated. Usually, however, induction of crystallization is achieved by means such as seeding, sound, stirring, or scratching the inner surface of the container. Typically, the concentrate is stirred with a propellor-type agitator for a period of time sufficient to cause crystallization of the enzyme at the prevailing temperature. Stirring as used here is intended to include all means of giving movement to the solution, and includes, but is not limited to, slow stirring, agitation (rapid stirring), and shaking, as well as the flowing movement of the solution during UF and/or evaporation.

Usually, stirring is conducted with a propellor-type blade spinning at 50 to 400 RPM (revolutions per minute) for 24 to 120 hours at a temperature of 5° C. to 60° C. Preferably, the stirring is done above room temperature. A typical temperature is 23° C.-32° C. A temperature around 25° C. and a time around 72 hours is most desired for alpha-amylase. The crystals precipitate and may be recovered by any known liquid/solid separatory technique such as centrifugation with decantation or filtration.

Heat stable alpha-amylase was obtained as follows: A nutrient medium suitable for fermentation of alpha-amylase can be prepared by adding the following ingredients to a 1,000 liter fermentor:

| Calcium Chloride Dihydrate | 0.2-1.0 kg |
| --- | --- |
| Mono- and Dipotassium Phosphate | 15-24 kg |
| Ammonium Sulfate | 2-7 kg |
| Sodium Citrate | 0-5 kg |
| A Sugar | 100-200 kg |
| Cotton Seed Meal | 25-40 kg |
| Soy Media | 30-50 kg |
| Antifoam | 8-13 liter |
| Water to: | 1,000 liter |

The medium was inoculated with viable cells of *Bacillus licheniformis* and allowed to ferment for 70-90 hours at 40°-45° C. while maintaining the pH at approximately netural. After this fermentation, the medium was flocculated with SEPARAN ® AP-30 ® to aid in biomass removal. SEPARAN AP-30 is a flocculant, the major ingredient of which is anionic polyacrylamide, supplied by Dow Chemical Company. The biomass was removed by centrifugation, and the centrate was polished by running it through Dicalite ® FW-6 (a diatomaceous earth supplied by Eagle Pitcher Company) precoated on a vacuum drum filter apparatus to provide 1000 liters of a cell-free filtrate having an activity of 50,000 MWU/ml as determined by the Manual Liquefying Alpha-Amylase Assay which is a modification of the method disclosed by Wohlgemuth in *Biochem.*, 29:1 (1908).

A nutrient medium suitable for alkaline protease fermentation can be prepared by adding the following ingredients to a 1000 liter fermentor:

| Soy Media | 50–100 kg |
|---|---|
| Sodium citrate | 4–5 kg |
| Calcium chloride dihydrate | 4–5 kg |
| A starch | 50–200 kg |
| Alpha-amylase | 40–55 gram |
| Mono and Disodium phosphate | 14–17 kg |
| Water to: | 1,000 liters |

The medium was inoculated with viable cells of *Bacillus licheniformis* and allowed to ferment for 30 to 48 hours at 35°–40° C. Whole beer fermentation broth (100 DAPU/gm) was diluted with water to 1500 liters. The pH was adjusted to 7.4 to 7.6 with 20% KOH, and then, the fermentation medium was flocculated by a suitable flocculant (SEPARAN AP-30) to aid in biomass removal. The biomass was removed by centrifugation and polished by running it through Dicalite precoated on a drum filter apparatus to provide 1500 liters of a cell-free filtrate containing 67 DAPU/ml as determined by the Detergent Alkaline Protease Assay which is a modification of the Delft Assay method developed by Royal Netherland Fermentation Industries, Ltd., Delft, Holland.

EXAMPLE I

Concentration by ultrafiltration of the TAKA-THERM alpha amylase cell-free filtrate having 50,000 MWU/ml activity was carried out in a Romicon HF-4 filter apparatus with a 10,000 molecular weight cut-off membrane at 10° C. to obtain a concentrate with a volume of 300 liters having an activity of 150,000 MWU/ml.

Concentration was continued by evaporation under vacuum in a flash evaporator (Buffalo single-stage forced circulation vacuum evaporator) with the pressure differential adjusted to 20 to 30 inches of Hg at 32° C. until the volume of the concentrate was down to 50 liters with an activity of 900,000 MWU/ml. This resulted in a supersaturated concentrate. The concentrate was adjusted to pH 7.6 using 20% KOH, and then stirred at 300 RPM with a propellor-type agitator for 72 hours at 25° C. resulting in the formation of enzyme crystals. The resulting enzyme crystals were recovered by centrifugation, and the excess liquid decanted. Enzyme yield in the crystals was 92% of the evaporate concentrate's total activity. The dry crystals from this example had an activity of 8,000,000 MWU/gm of dry material and 12,000,000 MWU/gm of protein.

EXAMPLE II

A 1000-liter TAKA-THERM filtrate was obtained from a fermentation similar to that used in Example I for the production of alpha-amylase crystals from the fermentation of *B. licheniformis*. The 1000 liter filtrate was concentrated to various fold values from 2 to 20 times concentration by UF at 10° C. using a Romicon filter apparatus with a 10,000 molecular weight cut-off membrane. The ultrafiltered concentrates were further concentrated by evaporation with a flash rotating evaporator (Brinkman-Buchi Rotovapor-R) at a temperature of 32° C. such that all the concentrates had an average initial concentrate activity approximately 650,000 MWU/ml, i.e. ranging from 565,000 to 738,000 MWU/ml. This resulted in a supersaturated concentrate. The pH of the concentrates was adjusted to 7.6 with 20% w/v KOH. The concentrates were stirred at 300 RPM with a motor driven mixer for 72 hours at room temperature (22° C.). The crystals and the supernatant were separated by centrifugation and decantation. The activity in the crystals and the supernatant were determined by the Modified Wohlgemuth (MWU) assay method, and are reported together with the initial concentrate activity in the Table below.

The 20 ml volumes sampled, recited in column 2, are included because they were used as the basis in determining the percent recovery, i.e. these initial values were designated as 100%. The volumes in column 4 are the volumes remaining of the supernatant after the enzyme crystals were removed. Thus, the enzyme activity in column 5 is the MWU/ml activity remaining in the supernatant after the crystals were removed, from which was calculated the percent enzyme activity recovery in the supernatant in column 6. The volumes in column 7 are the total volumes used after dissolving the enzyme crystals in H₂O, thus yielding the MWU/ml of enzyme activity of the crystals in column 8. Then the percent recovery of the crystals in column 9 is calculated in the usual method with the formula described at the bottom of the Table.

TABLE

| | Initial Concentrate | | | Supernatant | | | Crystal | |
|---|---|---|---|---|---|---|---|---|
| 1 | 2 | 3 | 4 | 5 | 6 | 7 | 8 | 9 |
| Fold (after UF) | Volume Sampled (ml) (after evaporation) | Activity MWU/ml | Volume (ml) | Activity MWU/ml | % Recovery | Volume (ml) Dissolved Crystals | Activity MWU/ml | % Recovery |
| 2.0 | 20 | 565,000 | 15 | 356,000 | 47 | 70 | 85,000 | 53 |
| 2.5 | 20 | 696,000 | 15 | 245,000 | 26 | 81 | 128,000 | 74 |
| 3.3 | 20 | 658,000 | 16 | 184,000 | 22 | 78 | 131,000 | 78 |
| 5.0 | 20 | 696,000 | 17 | 138,000 | 16 | 210 | 55,500 | 84 |
| 6.7 | 20 | 738,000 | 16 | 125,000 | 14 | 243 | 52,300 | 86 |
| 10.0 | 20 | 658,000 | 17 | 148,000 | 19 | 193 | 55,100 | 81 |
| 20.0 | 20 | 738,000 | 19 | 615,000 | 78 | 66 | 50,000 | 22 |

$$\% \text{ Recovery} = \frac{\text{Volume} \times \text{enzyme activity}}{\text{Volume of concentration} \times \text{enzyme activity of concentrate}}$$

Also, at an average initial concentrate activity of 600,000 MWU/ml, results are summarized graphically in the Figure. From this graph it can be seen that an average activity of 600,000 MWU/ml with 6.7-fold untrafiltration resulted in approximately 85%–86% of the enzyme being in crystallized form. Further ultrafiltration above 6.7-fold did not increase crystal formation, but rather crystallization falls off drastically as the Brix at 22° C. decreases. At 2-fold UF concentration with 600,000 MWU/ml, about 52%–53% of the enzyme was in crystalline form.

The Brix value indicates the amount of soluble solids present in solution in relation to sucrose as a standard. Therefore, the graph illustrates that ultrafiltration removes soluble solids that interfere with crystallization. If enough of the soluble solids are not removed, then TAKA-THERM cannot be evaporated to a high enough concentration for crystallization to occur. Rather, the solution will become so viscous that further evaporation cannot be conducted. The Brix values in the graph indicate the point at which enough soluble solids are removed so that evaporation may be continued far enough to obtain supersaturation for crystallization as used in the example.

EXAMPLE III

UF was carried out on the 1500 liters of alkaline protease cell-free filtrate containing 67 DAPU/ml activity at pH 7.4 to 7.6 in a Romicon HF-4 apparatus with a 2,000 molecular weight cut-off membrane at 10° C. to a volume of 250 liters at 400 DAPU/ml. This degree of UF removed enough soluble solids so that supersaturation was achieved. The Brix value was 10% at 20° C. Crystalization appeared to begin spontaneously without any further time and stirring. It is postulated that the movement as the solution was concentrated during UF was sufficient to induce crystallization without any further stirring by a means such as a propellor-type agitator The crystals were recovered by centrifugating and decanting the liquid phase. A small amount of crystalline enzyme was dissolved in water to determine activity, which was 63% of the ultrafiltered concentrate's total activity. The dry crystals from this example had an activity of 8,000 DAPU/gm dry material and 10,000 DAPU/gm of protein.

EXAMPLE IV

One thousand five hundred (1,500) liters of alkaline protease filtrate obtained from a fermentation as used in Example III were concentrated by UF in a Romicon HF-4 apparatus with a 2,000 molecular weight cut-off membrane at 10° C. to 500 liters at 200 DAPU/gm. Further concentration by evaporation was performed with a flash evaporator at 32° C. and 30 inches of mercury to 100 liters at 1,000 DAPU/gm. Crystals that were formed without any further time and stirring were recovered by centrifugating and decanting the liquid phase. A small amount of crystals were dissolved in water to determine activity, which was 85% of the ultrafiltered concentrate's total activity. The dry crystals from this example had an activity of 8,000 DAPU/gm dry material and 10,000 DAPU/gm protein.

As can be seen from comparing Examples III and IV, good recovery of 63% was achieved when concentration to supersaturation involved UF only as in Example III, but even better recovery of 85% was achieved when concentration to supersaturation involved UF and evaporation as in Example IV.

The terms used here are terms of description, not limitation. The use of such terms is not intended to exclude any equivalents of what is described here. It is recognized that modifications are possible within the scope of the claimed invention.

We claim:

1. A method for the recovery of an enzyme from its aqueous solution formed during the fermentation of an enzyme secreting bacteria in a suitable aqueous growth medium to form an enzyme solution containing biomass and other low molecular weight impurities from the fermentation of the bacteria which method consists essentially of the steps of:
   (a) subjecting the aqueous growth medium to liquid/solid separatory techniques to thereby separate the biomass from the liquid phase;
   (b) subjecting the liquid phase to ultrafiltration to thereby remove low molecular weight impurities; and
   (c) evaporating the liquid phase while maintaining the pH of the system at a level ±2.5 units from the isoelectric point of the enzyme to thereby bring the enzyme in solution to a point of supersaturation and precipitate the enzyme in the form of pure cyrstals.

2. The method of claim 1 wherein the pH is ±1.5 or less units from the isoelectric point.

3. The method of claim 1 wherein the solution is subjected to ultrafiltration at a temperature of 5° to 15° C. until its volume is approximately 10% to 50% of the starting volume followed by evaporation under a vacuum conducted at a temperature between 25° C. and 39° C. until the volume of the concentrate is approximately 10% to 20% of what it was after ultrafiltration.

4. The method of claim 1 wherein the enzyme is alpha-amylase and the pH is between 6.8 and 8.1.

5. The method of claim 1 wherein the enzyme is alkaline protease and the pH is between 8.0 and 10.0.

6. A method of recovering alpha-amylase secreted during the controlled fermentation of a bacterium of the species *Bacillus licheniformis* in a suitable aqueous growth medium to form an alpha amylase solution containing biomass and other low molecular weight impurities from the fermentation of the bacterium which method consists essentially of the stpes of:
   (a) Subjecting the aqueous growth medium to liquid/solid separatory techniques to thereby separate the biomass from the liquid phase;
   (b) subjecting the liquid phase to ultrafiltration at a temperature of from 5° to 15° C. until its volume is approximately 10% to 50% of the starting volume to thereby remove low molecular weight impurities; and
   (c) evaporating the liquid phase under vacuum at a temperature between 25° C. and 39° C. while maintaining the pH at a level between 6.8 and 8.1 until the volume of the concentrate is approximately 10% to 20% of what is was after ultrafiltration to thereby cause the alpha-amylase to precipitate in the form of pure crystals.

* * * * *